United States Patent [19]

Demmin et al.

[11] 4,329,498
[45] * May 11, 1982

[54] PREPARATION OF 6-AMINOCAPROIC ACID VIA MUCONIC ACID MONONITRILE

[75] Inventors: Timothy R. Demmin, Grand Island, N.Y.; Milorad M. Rogic, Whippany, N.J.

[73] Assignee: Allied Corporation, Morristown, N.J.

[*] Notice: The portion of the term of this patent subsequent to Jul. 7, 1998, has been disclaimed.

[21] Appl. No.: 243,226

[22] Filed: Mar. 13, 1981

Related U.S. Application Data

[63] Continuation-in-part of Ser. No. 74,442, Sep. 11, 1979, Pat. No. 4,277,419, which is a continuation-in-part of Ser. No. 942,507, Sep. 15, 1978, abandoned.

[51] Int. Cl.$^3$ .................... C07C 51/31; C07C 53/126; C07C 120/00; C07C 121/413
[52] U.S. Cl. ............................ 562/553; 260/239.3 R; 260/438.1; 260/465.4; 423/351; 423/371
[58] Field of Search ...................... 260/465.4; 562/553

[56] References Cited

U.S. PATENT DOCUMENTS

| | | | |
|---|---|---|---|
| 2,564,102 | 8/1951 | Fawcett et al. | 260/46.8 R |
| 3,062,869 | 11/1962 | Gould | 562/553 X |
| 3,632,625 | 1/1972 | aus der Funten et al. | 562/553 X |
| 3,988,319 | 10/1976 | Mares | 536/26 |
| 4,096,190 | 6/1978 | Rutledge | 568/730 |
| 4,277,419 | 7/1981 | Demmin et al. | 260/465.4 |

FOREIGN PATENT DOCUMENTS 1081469 3/1960 Fed. Rep. of Germany ...... 562/553

OTHER PUBLICATIONS

G. Vogel, J. Org. Chem., vol. 30, No. 1, pp. 203–207, (1965).
M. M. Rogic et al., J. Am. Chem. Soc., vol. 98, pp. 7441–7443, (1976).

*Primary Examiner*—Joseph Paul Brust
*Attorney, Agent, or Firm*—Alan M. Doernberg; Gerhard H. Fuchs

[57] ABSTRACT

Phenol, catechol and orthobenzoquinone are converted to muconic acid mononitrile by reaction with a copper-(II)-ammonia reagent. The copper(II)-ammonia reagents can be prepared by the reaction of cuprous chloride with oxygen or air in liquid ammonia or in ammonium hydroxide or in pyridine followed by addition of ammonia or ammonium hydroxide. Muconic acid mononitrile is hydrogenated to 6-aminocaproic acid, which can be cyclized to caprolactam.

17 Claims, No Drawings

PREPARATION OF 6-AMINOCAPROIC ACID VIA MUCONIC ACID MONONITRILE

CROSS-REFERENCE TO RELATED APPLICATIONS

This is a continuation-in-part of Ser. No. 074,442, filed Sept. 11, 1979, now U.S. Pat. No. 4,277,419, which was a continuation-in-part of Ser. No. 942,507, filed Sept. 15, 1978, now abandoned.

BACKGROUND OF THE INVENTION

Caprolactam is a widely used intermediate in the production of nylon-6 fibers, molding compounds and various plastic articles. Caprolactam is conventionally prepared by the reduction of phenol to cyclohexanone, oximation of cyclohexanone to cyclohexanone oxime and Beckmann rearrangement of cyclohexanone oxime to caprolactam. This method proceeds with high yields in all steps but employs hydroxylamine salts in various forms as the nitrogen source. Since preparation of a hydroxylamine salt solution from ammonia and other inorganic reagents can be difficult and expensive and can cause a large quantity of by-products, a need exists for a method of producing caprolactam and related amino acids without the use of hydroxylamine salts as intermediates.

The oxidative cleavage of phenol is known. Phenol can be oxidized successively to catechol (1,2-dihydroxybenzene), 1,2-benzoquinone and muconic acid monoesters. It has been reported that 4-tert-butyl-1,2-benzoquinone can be oxidized to a mixture of 3- and 4-tert-butylmuconic acid monomethyl esters by a copper(II) complex, pyridine cupric methoxy chloride in pyridine containing water. It has also been reported that phenol can be cleaved to cis,cis-muconic acid monomethyl ester in a system of pyridine cupric methoxy chloride complex and molecular oxygen.

It is also known that phenol, catechol and orthobenzoquinone can be oxidized with peracetic acid to cis,cis-muconic acid, which isomerizes, under certain conditions, to the cis,trans and trans,trans forms. The hydrogenation of muconic acid to adipic acid has also been reported. Adipic acid is commercially reacted with ammonia to form the corresponding diamide which is dehydrated and hydrogenated to hexamethylene diamine, the comonomer with adipic acid in nylon-66.

Copper-based materials are also known to catalyze the oxidative coupling of certain substituted phenols to diphenoquinones and biphenols as described, for example, in U.S. Pat. No. 4,096,190 to Rutledge (June 20, 1978). In certain examples of that patent, a copper salt and ammonia were suspended with stirring in water, a substituted phenol such as 2,6-xylenol (2,6-dimethyl phenol) was added and then oxygen flow was initiated. In example 12, the initial copper salt was cuprous chloride. It is not clear if, under such conditions, a copper(II)-ammonia reagent of the type described herein would be formed.

BRIEF DESCRIPTION OF THE INVENTION

It has been surprisingly found that phenol or catechol can be oxidatively cleaved in the presence of copper(II)-ammonia reagents to yield cis,cis-muconic acid mononitrile. The product can be hydrogenated to the commercially important 6-aminocaproic acid and caprolactam. Thus 6-aminocaproic acid and caprolactam can be made in a two-step process using easily available reagents and mild reaction conditions.

Thus, the present invention includes a process of producing 6-aminocaproic acid which comprises the steps:

(a) reacting phenol, catechol or orthobenzoquinone with a copper (II)-ammonia reagent in the liquid phase under reaction conditions forming cis,cis-muconic acid mononitrile or a copper salt thereof, (b) reacting the cis,cis-muconic acid mononitrile or copper salt thereof with hydrogen in the presence of a hydrogenation catalyst to form 6-aminocaproic acid.

DETAILED DESCRIPTION OF THE INVENTION

The oxidative cleavage of phenol and catechol with copper(II)-ammonia reagents proceeds under the mild conditions described herein to yield cis,cis-muconic acid mononitrile.

The copper(II)-ammonia reagent used herein is active to cleave phenol to cis,cis-muconic acid mononitrile in the presence of oxygen or air and to convert catechol (and presumably also orthobenzoquinone) to the same cis,cis-muconic acid mononitrile with or without air or oxygen being present. This material can be easily distinguished from the cis,trans or trans,trans isomer disclosed by George Vogel in *J. Org. Chem.* 30(1), pp. 203–207 (January 1965) in having a different melting point (136°–138° C. for the cis,cis isomer compared to 110°–111° C. for the cis,trans isomer and 175°–177° C. for the trans,trans isomer in the reference) and in not showing a trans-olefin band at 970 mm in the infrared and by other spectroscopic and analytical techniques.

Muconic acid mononitriles are themselves useful as monomers or comonomers for polymeric materials. More importantly, muconic acid mononitriles can be easily hydrogenated with Raney nickel, palladium, rhodium or other conventional hydrogenation catalysts to the corresponding 6-aminocaproic acids. In the case of the unsubstituted cis,cis-muconic acid mononitrile itself, the product, 6-aminocaproic acid, $NH_2-(CH_2)_5COOH$ can be cyclized to caprolactam, and the caprolactam or 6-aminocaproic acid, polymerized to nylon-6.

The cyclization of 6-aminocaproic acid can be accomplished by known techniques such as heating in an alcohol as described in U.S. Pat. No. 3,988,319 to F. Mares (issued Oct. 26, 1976). It is also possible to combine the hydrogenation and cyclization as by hydrogenating in ethanol with Raney nickel or other hydrogenation catalyst and then heating to 170°–200° C. to convert the dissolved 6-aminocaproic acid to caprolactam.

The muconic acid mononitriles can also be converted to substituted 6-aminocaproic acids by addition across the double bonds. For example, chloride or bromide can be introduced onto the carbon chain by addition of $Cl_2$ or $Br_2$ and then hydrogenation to form a halogenated 6-aminocaproic acid: $NH_2-CH_2-(CXH)_4COOH$ or the like, where X is Cl or Br. It will be appreciated that the halogenated 6-aminocaproic acid can be used as a comonomer to introduce flame retardancy into polyamides.

The starting material of the present process is phenol, catechol or orthobenzoquinone.

The copper(II)-ammonia reagents of the present invention may be prepared in several manners. First cuprous chloride may be oxidized by $O_2$ or air or other oxidizing agent in the presence of at least about equimolar amounts of ammonia or ammonium hydroxide. The reaction may occur in ammonia, in ammonium hydroxide or in an inert organic solvent such as one containing a nitrogen with an unshared electron pair such as pyridine, dimethyl formamide or N-methylpyrrolidone. Other such appropriate solvents may include diamines such as tetramethylethylenediamine and trialkylamines such as triethylamine. While the initial oxidation may occur in ammonium hydroxide, for example, it appears necessary that an organic compound having a nitrogen with an unshared electron pair must be added at some point to activate the material. Preferably such a material is present initially, especially as the solvent. In ammonium hydroxide the reaction may be seen to occur by the appearance of a blue color which is characteristic of copper(II). Different color changes characteristic of copper(II) formation occur in pyridine: bright yellow to black-brown on oxidation, then black-brown to black-green on ammonia addition. While the ratios of cuprous chloride to oxidizing agent to ammonia or ammonium hydroxide are not critical, the oxidizing agent is preferably present in at least stoichiometric amounts compared to copper(I) (a 1:4 mole ratio in the case of $O_2$). Ammonia or ammonium hydroxide is preferably present in at least about a 1:1 mole ratio to copper preferably at least about 2:1, with excesses and even large excesses of ammonia or ammonium hydroxide being also preferred. The temperature of the oxidation of cuprous chloride is not critical, and it may be conveniently performed at $-60°$ to $+50°$ C., depending upon the solvent used. The preferred temperature for oxidation of copper(I) in liquid ammonia is $-60°$ to $-50°$ C. The preferred temperature for oxidation of copper (I) in pyridine or ammonium hydroxide is room temperature (such as $15°-30°$ C.).

The copper(II)-ammonia compositions or reagents of the present invention may also be prepared by oxidizing copper metal in pyridine or ammonium hydroxide to a copper(II) oxide which is inactive by Electron Spin Resonance Spectroscopy and is believed to possess paired spins and resemble the dimer formula:

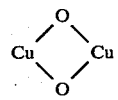

and reacting the copper(II) oxide with at least about equimolar amounts of ammonium hydroxide or ammonia, i.e. at least about a 1:1 $NH_3$:Cu molar ratio. The oxidation of copper metal is conducted in the presence of at least catalytic amounts of a copper salt such as cuprous chloride or cupric chloride causing the following proposed sequence in the case of chloride salts:

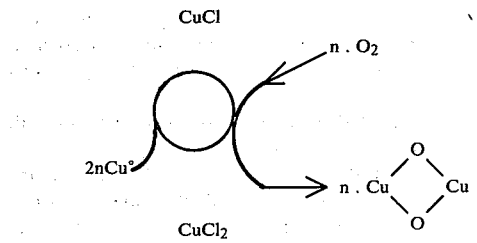

Since the copper chlorides are not consumed, pure copper metal can be continually added, producing a mixture low in copper chlorides.

The oxidation of copper metal or of cuprous chloride may be conducted in pyridine (or similar solvent) or ammonia or ammonium hydroxide. If either oxidation is conducted in pyridine, ammonia or ammonium hydroxide can either be present during oxidation, or preferably, added after oxidation.

The copper(II)-ammonia compositions or reagents of the present invention may also be prepared by reacting pyridine cupric methoxy chloride complex, a known material described by Hays et al. In *J. Am. Chem. Soc.*, vol. 81, p. 6335 (1959), with ammonia or ammonium hydroxide. In the presence of water alone the pyridine cupric methoxy chloride in pyridine is active to form muconic acid monomethyl ester as described in our Communication in *J. Am. Chem. Soc.*, vol. 98, pp. 7441–7443 (1976). Free methanol may be removed from the copper(II)-ammonia reagent, as by evaporation, so that the reagent can, in some cases, produce more mononitrile and less monoester when reacted with the cyclic starting material.

In the foregoing discussion, copper(I) chloride is described as the CuX starting material. Salts of copper(I) and other monovalent anions such as I, Br, acetate and benzoate may also be used, however, to prepare copper(II)-ammonia reagents which are also active to convert cycling starting materials to muconic acid mononitriles, but not necessarily to the same degree. Thus, for example, reagents formed from CuBr are generally comparable in activity to those formed from CuCl, while reagents formed from CuI appear somewhat less active. Other soluble copper(I) salts such as copper(I) acetate and copper(I) benzoate may also be used by oxidizing them with oxygen and adding ammonia or ammonium hydroxide to the product.

The copper(II)-ammonia reagents of the present invention are useful not only to cleave phenols, catechols and orthobenzoquinones to muconic acid mononitriles, but also to convert various aldehydes to nitriles. It is possible that the conversion of an aldehyde to a nitrile may form a part of the mechanism of the overall phenol cleavage reaction.

The present invention is thus contemplated to include active copper(II)-ammonia reagents prepared by each of the above techniques which are believed to represent novel methods as well. It is not asserted that the identical reagent is prepared by each of the above techniques, and in fact there is some evidence that different methods produce different but analogous reagents which cause different product mixtures in some cleavage reactions.

In general, the active copper(II)-ammonia reagent can be characterized by the empirical formula, when recovered from a solvent, of $(CuO)(CuX_2)_y(NH_3)_z$ where x is a monovalent anion such as Cl, Br, I, acetate or benzoate; y is between about 0.2 and about 1 and z is between about 2 and 4.

Unless extraordinary measures are taken during preparation to enhance the CuO component relative to the $CuX_2$ component, they will generally be about equimolar such that the empirical formula becomes $Cu_2OX_2(NH_3)_z$. When z is less than 4 (or less than two times the moles of copper in the more general formula), the difference is normally made up by ligands of the organic nitrogen-containing solvent.

Representative copper(II)-ammonia reagents thus have the following empirical formulae:

$Cu_2OCl_2(NH_3)_4$ $Cu_2OBr_2(NH_3)_4$ $Cu_2OCl_2(NH_3)_3(py)$ $Cu_2OCl_2(NH_3)_3(DMF)$ $Cu_2OBr_2(NH_3)_3(py)$ $Cu_{1.5}OBr(NH_3)_3$ $Cu_2OI_2(NH_3)_4$ $Cu_2O(CH_3COO)_2(NH_3)_4$

It should be appreciated that the active reagent itself need not be soluble in the solvent employed, but may instead be suspended (preferably in very small particles) in the solvent. Thus, for example, when CuCl is oxidized, the resulting mixture of copper(II) oxide and copper(II) chloride is soluble in, for example, pyridine. When ammonia is added, however, the active reagent precipitates in fine particles forming a suspension that is active for the conversion of a catechol to a muconic acid mononitrile. As shown by the examples, this suspension can be separated from the solvent, and an aliquot characterized as to empirical formula, and then the precipitate resuspended in an appropriate solvent and used to convert a catechol to a muconic acid mononitrile.

In the reaction mixture which includes the cyclic starting material, copper is preferably less than about 0.5 molar (regardless of solvent) because more concentrated copper can cause polymerization. More preferred is about 0.05 to about 0.2 molar copper.

The copper(II)-ammonia reagent is preferably present in at least about stoichiometric amounts compared to the cyclic starting material. In theory, the cleavage of quinones is a two electron oxidation, the cleavage of catechols is a four electron oxidation and the cleavage of phenols is a six electron oxidation. Accordingly, molar ratios of copper starting material of 2:1, 4:1 and 6:1 might appear necessary for quinones, catechols and phenols respectively. Under aerobic conditions, however, oxygen may oxidize cyclic starting material or reduced forms of copper formed during the reaction. Accordingly, lower molar ratios (especially lower than 6:1 for phenols) may be in excess of stoichiometric amounts under actual conditions. At present, molar ratios of at least 2:1 are preferred for all starting materials.

When less than a 2:1 molar ratio of copper(II) ammonia reagent to starting material is used, a lesser amount of the starting material would be converted to product unless inorganic copper salts are recovered from the product and converted back to the copper(II)-ammonia reagent.

The preferred temperature range for the cleavage reaction is between about 15° C. and about 35° C., with a suitable overall range being about 0° C. to about 50° C. Temperatures much below room temperature are less preferred for phenols because the reaction is slowed down. Temperatures much above room temperature are somewhat less preferred for all starting materials because of a possible increase in polymerization rates of the reagent or the organic materials and thus lowered yields. While the reaction may be performed at atmospheric pressure or below, superatmospheric pressures can cause increased reaction rates, especially for phenols.

The reaction mixture after the oxidative cleavage reaction contains copper salts of muconic acid mononitriles which, if oxygen is added during reaction, appear to be copper(II) salts and, if oxygen is not present during reaction, appear to be mixtures of copper(I) salts and copper(II) salts. The reaction mixture also usually contains other copper-containing materials including, perhaps, a form of copper(II) chloride in the reaction mixture when copper(I) chloride is the original copper source and oxygen is present in excess during the reaction. The copper salt or salts of muconic acid mononitrile can be concentrated by filtering out the suspended copper salts and evaporating off the solvent. If one desires to purify the copper(II) salts further, one would then purify the residue by conventional techniques such as recrystallization from a suitable solvent which could be dimethyl formamide, acetonitrile, pyridine or a suitable combination of these solvents, or by a suitable chromatography technique.

To recover the muconic acid mononitrile itself, the crude copper salts of muconic acid mononitrile are hydrolyzed with an inorganic acid; and the muconic acid mononitrile is extracted into an organic layer. In some of the following examples these steps are combined by adding HCl in ether. Filtration after acidification and addition of the organic solvent produces solid salts (which appear to be copper(II) chloride when copper(I) chloride is the copper source, oxygen is added during reaction and HCl is the acid used for hydrolysis) and a filtrate of the muconic acid mononitrile in the organic solvent. The mononitrile can be recovered from the filtrate by evaporating off the solvent. If care is taken to exclude oxygen from this work-up, the valence of the solid copper salts filtered out in the last step should be indicative of the valence of copper in the copper salts of muconic acid mononitrile originally formed. Based upon the appearance of the solid copper salts recovered from most work-ups, it appears that the original copper salts are copper(II) salts in the presence of excess oxygen but can be caused to include at least a portion of copper(I) salts if the oxygen present during the reaction is limited.

As illustrated by the Examples that follow, the initial product mononitrile is in the cis,cis-configuration when unsubstituted, but can contain other isomers even in major proportions under certain conditions when substituted as by a tertiary butyl group. If it is desired to separate these isomers, this can be accomplished by conventional chromatographic techniques. If it is desired to produce cis,trans or trans,trans isomers from an initial cis,cis isomer, this ought to be accomplished by conventional techniques such as heating the nitrile in the molten state or subjecting the nitrile in solution to an appropriate isomerizing radiation. Such isomerization of muconic acid itself is described in an article entitled, "The Third Isomeric (cis-trans-) Muconic Acid" by J. A. Elvidge et al. at *J. Chem. Soc.* pp. 2235–41 (1950). This article demonstrates that cis,cis-muconic acid is readily inverted to cis,trans-muconic acid (as by crystallization from boiling water) and that both the cis,cis and cis,trans isomers can be isomerized to the trans,trans isomer by irradiation by ultraviolet light in water containing a trace of iodine. No evidence is presented that the reverse inversions of muconic acid (trans,trans to either other form or cis,trans to cis,cis) takes place.

EXAMPLE 1—PHENOL AS REACTANT—AMMONIA

Cuprous chloride (60 grams, 600 millimoles) in about 300 milliliters of liquid ammonia at −55° C. was oxidized with molecular oxygen for 2-3 hours to give a dark heterogenous mixture. Dry pyridine (3000 mL) was added and, under nitrogen, the mixture was warmed to 0° C. with loss of excess ammonia. Oxygen and ammonia were bubbled through the vigorously stirred mixture and phenol (14.1 grams, 150 millimoles) in about 30 mL of pyridine was added. The mixture was warmed to room temperature and maintained there for a total of 16 hours with stirring and continued ammonia and oxygen introduction. The mixture was then evaporated under vacuum at 25°-30° C. and the solid residue extracted with 600 mL of diethyl ether followed by filtration. Evaporation of ether from the liquid gave 8.4 grams of phenol with a trace of green copper salts and pyridine. The green-black solid filtrate was suspended in 600 mL of ether and cooled to 0° C. with stirring. HCl was added in the form of 125 mL of ether saturated with HCl over 15 minutes, with constant stirring, followed by 30 minutes of additional stirring at 0° C. The yellow solid (apparently impure copper(II) chloride) was then filtered out and the filtrate (dark red solution) dried and evaporated to 5.3 grams of a brown solid. Analysis of the brown solid by n m r indicated about half cis,cis-muconic acid mononitrile and about half phenol, representing a 24% conversion and a 60% yield.

EXAMPLE 2-12

The process of Example 1 was varied as described in the description of Examples 2-12 in parent application Ser. No. 074,442, the disclosure of which is incorporated herein by reference. These Examples are summarized in Table I, below, wherein the following abbreviations are used:

4TBP=4-tert-butylphenol
4TBC=4-tert-butylcatechol
4TBQ=4-tert-butyl-o-benzoquinone
PyCuOMeCl pyridine complex of copper methoxy chloride All Examples except 12 were conducted at atmospheric pressure. The work-up varied slightly as to the solvent (ether or methylene chloride) in which HCl was added.

As indicated in the parent application, ammonia or ammonium hydroxide were present during copper oxidation or added after copper oxidation in each of examples 2-12. Examples 5-7 and 9 are included to show the analogous production of t-butylmuconic acid mononitrile, which is not within the scope of part a of the present process.

TABLE I

| Ex | SM | Cu | Conversion | Yield | Comments |
|---|---|---|---|---|---|
| 1 | Phenol | CuCl | 24% | 60% | |
| 2 | Phenol | CuCl | 74 | 39 | small amounts phenyl esters |
| 3 | Phenol | CuCl | 71 | 57 | trace of phenyl esters |
| 4 | Phenol | CuCl | 77 | 23 | no phenyl esters |
| 5 | 4TBP | CuCl | 65 | 19 | only one isomer |
| 6 | 4TBC | PyCuOMeCl | complete | | 3 isomers + "cyclic" |
| 7 | 4TBQ | PyCuOMeCl | complete | | 3 isomers + "cyclic" |
| 8 | Catechol | PyCuOMeCl | complete | about 40 | trace of mono-methyl ester |
| 9 | 4TBC | CuCl | complete | about 50 | one main product, small amounts other isomer and by-products |
| 10 | Catechol | CuCl | complete | 26% | |
| 11 | Catechol | CuCl | complete | about 25% | |
| 12 | Phenol | CuCl | 65% | 24% | Cleavage at 60 psig pressure of oxygen |

EXAMPLE 13—HYDROGENATION WITH RANEY NICKEL

Cis,cis-muconic acid mononitrile (0.5 grams) prepared as in Example 1 was dissolved in 250 mL of dry ethanol saturated with ammonia. Excess Raney Nickel was added and the stirred solution treated with $H_2$ (at 1000 psi gage or about 7 MPa absolute pressure) for 15 hours at room temperature. Excess catalyst was removed by filtration and the solution evaporated to dryness. Remaining catalyst was removed by adding about 5 mL water and filtering. Evaporating the aqueous layer gave about 0.5 grams of an off white solid identified by infrared and n m r as 6-aminocaproic acid.

Based upon the known process of Mares, it would be expected that heating the 6-aminocaproic acid in ethanol before isolation to about 170°-200° C. would result in cyclization. It would also be expected that the crude product of cleavage before hydrolysis (probably the copper salt of muconic acid mononitrile) could be directly hydrogenated to 6-aminocaproic acid.

EXAMPLE 14—HYDROGENATION WITH RHODIUM

When example 13 is repeated using glacial acetic acid as solvent and 5% rhodium on carbon as catalyst, 6- aminocaproic acid was obtained in similar yield, but with easier separation of product and catalyst.

PHYSICAL DATA

The following data for cis,cis-muconic acid mononitrile (cis-5-cyano-cis-2,4-pentadienoic acid) was obtained from the products of several different Examples (1-4, 8 and 10-12). In each above Example, ir and nmr spectra were performed to analyze for the product. The other physical data were obtained only on some specimens.

Melting point—136°–138° C.

Ultraviolet $\lambda_{max}CH_3CN$ 259 nm ($\epsilon$15,900), 290 nm (sh) $\lambda_{max}MeOH$ 257 nm ($\epsilon$16,100)

Infrared (NUJOL) 3350–2230 ($CO_2H$), 2215 (—CN), 1775 ($CO_2H$), 1675 (shoulder), 1621, 1564, 1452, 1347, 1305, 1262, 1198, 921, 840, 782, 693 and 667.

NMR (($CD_3)_2CO$): $\delta$5.78 (d of t, 11 and <1 Hz,=CH—$CO_2$—, 1), 6.12 (d of t, 11 and <1 Hz, =CH—CN, 1), 7.00 (t of d, 11 and <1 Hz, —CH=C—CN, 1), 8.13 (t of d, 11 and <1 Hz, —CH=C—$CO_2$-, 1) and 9.85 (bs, $CO_2H$, 1). These tentative assignments are internally consistent based on decoupling experiments.

CMR ($CDCl_3$) $\delta$105.47 (=$\underline{C}$H—CN), 115.09 (—CN), 124.83 (=CH—$CO_2$—), 139.11 (—$\underline{C}$H=C-CN), 142.97 (—$\underline{C}$H=C—$CO_2$) and 169.81 (—$CO_2H$).

ANAL $C_6H_5NO_2$; Calc: C, 58.53; H, 4.09; N, 11.38; Found: C, 58.83; H, 4.18; N, 11.17.

Mass Spec (C.I./$NH_3$): 124 for molecule plus a proton (thus molecular weight is 123).

EXAMPLES 15–25

The description of Examples 15–25 of parent application Ser. No. 074,442 is incorporated herein by reference for a disclosure of processes similar to Example 1 in which active copper (II) ammonia reagents were made, isolated and then resuspended and used to cleave 4-tert-butyl catechol to isomers of tert-butyl muconic acid mononitrile. These examples are summarized in the following Table II.

TABLE II

| Example | CuX | Solvent for Cu oxidation | Isolated | Solvent for cleavage |
|---|---|---|---|---|
| 15 | CuCl | pyridine | yes | — |
| 16 | from example 15 | — | pyridine |
| 17 | from example 15 | — | dimethylformamide |
| 18 | CuCl | dimethylformamide | no | dimethylformamide |
| 19 | CuCl | N-methylpyrrolidone | no | N-methylpyrrolidone |
| 20 | CuBr | pyridine | yes | — |
| 21 | CuI | pyridine | yes | — |
| 22 | CuBr | pyridine | no | pyridine |
| 23 | CuI | pyridine | no | pyridine |
| 24 | CuCl | pyridine* | yes | — |
| 25 | from example 24 | — | pyridine |

*in example 24 ammonium hydroxide was used instead of ammonia after CuCl was oxidized in pyridine Although each of examples 16–19, 22, 23 and 25 employ 4-tert butyl catechol rather than catechol, and are thus outside the scope of part a of the present process, they do show a range of copper (I) salts, oxidation solvents and cleavage solvents which would also be useful in the analogous reaction of catechol, which analogous reaction is within the scope of part a of the process of the present invention.

We claim:

1. A process of producing 6-aminocaproic acid which comprises:
   (a) reacting phenol, catechol or orthobenzoquinone with a copper(II)-ammonia reagent in the liquid phase under reaction conditions forming cis, cis-muconic acid mononitrile or a copper salt thereof,
   (b) reacting the muconic acid mononitrile or copper salt thereof with hydrogen in the presence of a hydrogenation catalyst to form 6-aminocaproic acid;

said copper(II)-ammonia reagent being selected from the group consisting of
   (i) a copper(II)-ammonia reagent prepared by the oxidation of a soluble cuprous salt in the presence of at least about equimolar amounts of ammonia or ammonium hydroxide;
   (ii) a copper(II)-ammonia reagent prepared by the oxidation of a soluble cuprous salt with oxygen in an organic solvent having a nitrogen with an unshared electron pair and then adding ammonia or ammonium hydroxide in a molar amount at least twice the moles of cupric ion, and
   (iii) a copper(II)-ammonia reagent suspended in an organic solvent having a nitrogen with an unshared electron pair, wherein the copper(II)-ammonia reagent, when recovered from the organic solvent, has an empirical formula $(CuO)(CuX_2)_y(NH_3)_z$

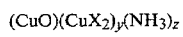

where X is a monovalent anion, y is between about 0.2 and about 1 and z is between about 2 and about 4.

2. The process of claim 1 wherein phenol is reacted with the copper(II)-ammonia reagent in the presence of excess oxygen.

3. The process of claim 1 wherein catechol is reacted with the copper(II)-ammonia reagent.

4. The process of claim 1 wherein step (a) is conducted in the presence of an organic compound having a nitrogen with an unshared electron pair.

5. The process of claim 4 where step (a) is conducted in pyridine solvent.

6. The process of claim 1 wherein the reaction mixture in step (a) is less than about 0.5 molar in copper.

7. The process of claim 6 wherein said reaction mixture is about 0.05 to about 0.2 molar in copper.

8. The process of claim 1 wherein the copper(II)-ammonia reagent is prepared by the oxidation of a soluble cuprous salt in the presence of at least about equimolar amounts of ammonia or ammonium hydroxide.

9. The process of claim 1 wherein the copper(II)-ammonia reagent is prepared by the oxidation of a soluble cuprous salt with oxygen in an organic solvent having a nitrogen with an unshared electron pair and then adding ammonia or ammonium hydroxide in a molar amount at least twice the moles of cupric ion.

10. The process of claim 9 wherein the organic solvent is pyridine.

11. The process of claim 9 or 10 wherein the soluble cuprous salt is cuprous chloride.

12. The process of claim 1 wherein the copper (II)-ammonia reagent is suspended in an organic solvent having a nitrogen with an unshared electron pair and wherein the copper(II)-ammonia reagent, when recovered from the organic solvent, has an empirical formula $(CuO)(CuX_2)_y(NH_3)_z$

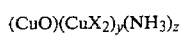

where X is a monovalent anion, y is between about 0.2 and about 1 and z is between about 2 and about 4.

13. The process of claim 12 wherein said empirical formula is $Cu_2OX_2(NH_3)_z$.

14. The process of claim 12 or 13 wherein X is selected from the group consisting of chloride, bromide and iodide.

15. The process of claim 14 wherein the organic solvent is pyridine.

16. The process of claim 12 or 13 wherein the organic solvent is pyridine.

17. The process of claim 1 or 2 or 4 or 8 or 9 or 12 or 13 wherein the hydrogenation catalyst is Raney nickel.

* * * * *